US012312952B2

(12) United States Patent
Song et al.

(10) Patent No.: US 12,312,952 B2
(45) Date of Patent: May 27, 2025

(54) WHOLE-PROCESS MULTI-PARAMETER MONITORING DEVICE AND METHOD FOR SIMULATING $CO_2$ GEOLOGICAL SEQUESTRATION AND USE THEREOF (71) Applicant: DALIAN UNIVERSITY OF TECHNOLOGY, Liaoning (CN)

(72) Inventors: Yongchen Song, Liaoning (CN); Lei Yang, Liaoning (CN); Mingjun Yang, Liaoning (CN); Yu Liu, Liaoning (CN); Lanlan Jiang, Liaoning (CN); Dawei Guan, Liaoning (CN); Lunxiang Zhang, Liaoning (CN); Yi Zhang, Liaoning (CN); Yanghui Li, Liaoning (CN); Zheng Ling, Liaoning (CN); Tao Yu, Liaoning (CN); Bingbing Chen, Liaoning (CN); Peng Wu, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 18/784,963

(22) Filed: Jul. 26, 2024

(65) Prior Publication Data
US 2025/0034995 A1 Jan. 30, 2025

(30) Foreign Application Priority Data
Jul. 28, 2023 (CN) .......................... 202310941965.X (51) Int. Cl.
*G01N 33/00* (2006.01)
*E21B 43/16* (2006.01)
(Continued)

(52) U.S. Cl.
CPC .......... *E21B 49/008* (2013.01); *E21B 43/164* (2013.01); *E21B 47/07* (2020.05); *E21B 2200/20* (2020.05); *G01N 33/00* (2013.01)

(58) Field of Classification Search
CPC ...... E21B 49/008; E21B 43/164; E21B 47/07; E21B 2200/20
See application file for complete search history.

(56) References Cited

U.S. PATENT DOCUMENTS 11,834,933 B1 * 12/2023 Stewart .................. C09K 8/594
2023/0200360 A1 * 6/2023 Chang .................. E21B 41/005
405/195.1
(Continued)

FOREIGN PATENT DOCUMENTS

CN 103927913 B * 5/2016
CN 108037016 A * 5/2018 ......... G01N 15/0806
(Continued)

OTHER PUBLICATIONS

Ranjith et al. "A new triaxial apparatus to study the mechanical and fluid flow aspects of carbon dioxide sequestration in geological formations" (Year: 2011).*
(Continued)

*Primary Examiner* — Eyob Hagos
(74) *Attorney, Agent, or Firm* — Ming Jiang; OPENPTO US LLC (57) ABSTRACT

The present disclosure relates to the field of $CO_2$ geological sequestration, and provides a whole-process multi-parameter monitoring device and method for simulating $CO_2$ geological sequestration and use thereof. A large-scale reactor body is developed, and a geological reservoir at a depth of 800 to 3000 meters is simulated. A modular built-in model device is researched and developed, a multi-type and variable-structure reservoir remodeling technology is developed, and mutual coupling of modules can be achieved. The
(Continued)

design idea of separating the pressure reactor from the built-in sample model is adopted in the device. The confining pressure, the pore pressure, the temperature gradient, and the axial load of the device can be independently controlled through a temperature control mechanism and a loading mechanism respectively, so that the restoration of the state of in-situ stresses in the reservoir is realized.

11 Claims, 5 Drawing Sheets

(51) Int. Cl.
*E21B 47/07* (2012.01)
*E21B 49/00* (2006.01)

(56) References Cited

U.S. PATENT DOCUMENTS

| 2023/0323755 | A1* | 10/2023 | Al-Qasim | E21B 43/164 166/402 |
| 2024/0167991 | A1* | 5/2024 | Sayed | G01N 33/004 |
| 2024/0328283 | A1* | 10/2024 | Duncan | E21B 43/164 |
| 2025/0003313 | A1* | 1/2025 | Jones | E21B 41/0064 |

FOREIGN PATENT DOCUMENTS

| CN | 110618255 | | 12/2019 | |
| CN | 110618255 A | * | 12/2019 | E21B 47/06 |
| CN | 115078102 A | * | 9/2022 | G01L 13/00 |

OTHER PUBLICATIONS

Kehua Su et al., "A large-scale three-dimensional device for simulating natural gas hydrates accumulation and distribution process in sediments", Natural Gas Industry, vol. 33, Dec. 2013, pp. 173-178.

* cited by examiner

WHOLE-PROCESS MULTI-PARAMETER MONITORING DEVICE AND METHOD FOR SIMULATING $CO_2$ GEOLOGICAL SEQUESTRATION AND USE THEREOF

CROSS-REFERENCE TO RELATED APPLICATION

This application claims the priority benefit of China application serial no. 202310941965.X, filed on Jul. 28, 2023. The entirety of the above-mentioned patent application is hereby incorporated by reference herein and made a part of this specification.

BACKGROUND

Technical Field

The present disclosure relates to the field of $CO_2$ geological sequestration, and particularly to a whole-process multi-parameter monitoring device and method for simulating $CO_2$ geological sequestration, and use thereof in $CO_2$ sequestration.

Description of Related Art

With the rapid development of the global economy and the massive consumption of fossil energy, greenhouse gas emissions are increasing year by year, resulting in global warming and a series of ecological and environmental problems. In 2021, fossil energy accounted for 83.4% of the total energy supply in China, with $CO_2$ emissions generated by combustion of fossil energy accounting for at least 80% of the total $CO_2$ emissions. Although the proportion of new energy and even zero-carbon energy has increased in recent years, the green transformation of energy is a long-term process. Carbon dioxide Capture Utilization and Storage (CCUS) is not only a strategic choice to ensure energy security in China, but also an important means to build ecological civilization and achieve sustainable development. $CO_2$ geological sequestration is the main step of CCUS, and is also one of the most effective ways to deal with climate change in China. The $CO_2$ sequestration process involves multi-phase, multi-component, and multi-dimensional complex physical and chemical processes. Physical experimental devices are usually used to simulate the geological sequestration process, and the $CO_2$ sequestration mechanism is revealed by monitoring the phenomena that occur in the mock objects. At present, conventional small-scale reactors are greatly affected by the boundary effect due to the small size, and cannot reflect the reservoir state in all dimensions. The boundary effect means that because the distances of gas and water transport and heat transfer in the small-scale reactors are short, the reaction may be faster, and the mass and heat transfer efficiency may be higher. In addition, the surface area of the small-scale reactor is relatively large, which may lead to more surface reactions and higher surface reaction rates, resulting in a large difference between the simulated sequestration state in the reactor and the actual reservoir. On the contrary, in large-scale reactors, the distances of gas and water transport and heat transfer are longer due to the larger size, and it takes a longer time to achieve equilibrium. In addition, the large volume of large-scale reactors also limits the range of contact of gas and water with substances, leading to a decrease in the reaction rate. Therefore, the actual reservoir in the process of geological sequestration can be more accurately reflected by constructing a large-scale mock reactor. However, large-scale reactors are difficult to manufacture, cannot be put into use in a timely manner, and cannot simulate all-round changes of the confining pressure and the axial pressure of the reservoir. To solve the above difficulties, it is urgent to develop a large-scale high-pressure reactor device capable of heat-pressure-force-sound-light-electricity multi-dimensional monitoring, which allows for the use of independent functional modules in combination according to the actual situation to meet the requirement for large simulation scale and flexibly simulate the complex geological structure of reservoirs in multiple dimensions. Moreover, this device integrates multi-physical-field multi-dimensional detection technologies, has an improved arrangement of distributed sensors, and can accurately obtain parameters related to the pressure field, temperature field, flow field, and stress field during the simulation experiment.

SUMMARY

To overcome the difficulties in the prior art, the present disclosure provides a whole-process multi-parameter monitoring device and method for simulating $CO_2$ geological sequestration and use thereof. The device adopts the design idea of separating the large-scale pressure reactor from the built-in sample model, and the confining pressure, the pore pressure, the temperature gradient and the axial load of the device can be independently controlled through a temperature control mechanism and a loading mechanism respectively, to achieve mutual coupling of the modules. The device can realize the restoration of the in-situ stress of the reservoir, and adopts a novel heat-pressure-force-sound-light-electricity multi-means joint test method to obtain the real-time changes of various parameters in the reservoir during $CO_2$ sequestration and evaluate the characteristics of the reservoir for sequestration in real time from multiple perspectives and dimensions, providing more detailed theoretical guidance for $CO_2$ field sequestration.

The following technical solutions are employed in the present disclosure.

A whole-process multi-parameter monitoring device for simulating $CO_2$ geological sequestration is provided, including a high-pressure reactor, a temperature control system, a fluid injection system, and a multi-physical field detection system, where the temperature control system is configured to control an ambient temperature and an internal temperature of the high-pressure reactor;

the fluid injection system is configured to inject different types of fluids into the high-pressure reactor;

the high-pressure reactor includes a reactor cover, a reactor body, a confining pressure rubber bucket, and a plug assembly; the reactor cover is arranged above the reactor body, and the reactor cover is fixedly connected to an outer portion of the reactor body by a snap ring; the confining pressure rubber bucket is a bucket-shaped structure having an upper opening and a lower opening and is arranged inside the reactor body, an upper edge of the confining pressure rubber bucket is sealedly connected to a lower end of the reactor cover, and a lower edge of the confining pressure rubber bucket is sealedly connected to the plug assembly; a confining pressure chamber is formed by the confining pressure rubber bucket, the plug assembly, and the reactor body; and the multi-physical field detection system includes different types of sensors arranged on the reactor cover, the reactor body, and the confining pressure rubber bucket to implement multi-dimensional detection.

Further, the plug assembly includes a plug cylinder and a plug piston assembly; the lower edge of the confining pressure rubber bucket is sleeved on and sealedly connected to an outer periphery of the plug cylinder; the plug piston assembly is arranged in an upper portion of the plug cylinder, an outer wall of the plug piston assembly is in close contact with and sealedly connected to an inner wall of the plug cylinder, and a hydraulic oil cavity for accommodating a hydraulic oil is formed between a lower portion of the plug piston assembly and the plug cylinder; a piston hydraulic interface is arranged at a bottom of the plug cylinder, and axial stress loading is controlled by an axial pressure tracking pump; and the plug piston assembly is provided with a channel in communication with the fluid injection system, and the channel is configured to inject a fluid required for simulating the $CO_2$ geological sequestration to the confining pressure rubber bucket.

Further, a cavity is provided above the plug piston assembly, and a porous plug plate and a filter plate covering a bottom section of the confining pressure rubber bucket are arranged above the cavity in sequence from bottom to top; the porous plug plate is provided with holes uniformly drilled thereon, and is configured to support a porous medium; a pore size of the filter plate prevents the porous medium from leaking out of the porous plug plate; a heating circulation pipe is arranged in the cavity to control a ground temperature gradient; and a supporting column is arranged between a bottom of the cavity and the porous plug plate to prevent a sand-filled sample from damaging the heating circulation pipe.

Further, the plug assembly further includes a copper sleeve wear-resistant ring, the copper sleeve wear-resistant ring is sheathed in a groove on an outer wall surface of the plug piston assembly, and a guide groove is provided on an outer periphery of the copper sleeve wear-resistant ring to prevent the plug piston assembly from deviating during movement relative to the plug cylinder to cause dislocation of the filter plate and jamming of the plug piston assembly.

Further, a gas injection column is arranged in the cavity above the plug piston assembly, a gas injection transfer pipe is arranged in a cavity below the plug piston assembly, a first end of the gas injection transfer pipe is connected to the gas injection column, and a second end of the gas injection transfer pipe is connected to a gas injection module in the fluid injection system for injecting gas into a reservoir; and a heat injection circulation transfer pipe is further arranged in the cavity below the plug piston assembly, a first end of the heat injection circulation transfer pipe is connected to the heating circulation pipe, a second end of the heat injection circulation transfer pipe is connected to a temperature control water bath, and the heat injection circulation transfer pipe is configured to simulate the ground temperature gradient and control a vertical temperature gradient.

Further, both the gas injection transfer pipe and the heat injection circulation transfer pipe are spirally shaped to prevent damage to pipelines during displacement.

Further, the plug cylinder is sealedly connected to the plug piston assembly by a piston seal assembly, and the lower edge of the confining pressure rubber bucket is sealedly connected to the outer periphery of the plug cylinder by the piston seal assembly; a first end of a pre-tightening pull rod is mounted on the plug cylinder and a second end of the pre-tightening pull rod is connected to the reactor cover to prevent components from falling when a built-in model is taken out from a built-in model overturning mechanism, and the built-in model mainly includes the reactor cover, the confining pressure rubber bucket, and the plug assembly; the piston seal assembly is in the form of a combination of two support rings and an O-shaped sealing ring, and is configured to prevent the hydraulic oil in a hydraulic oil cylinder from leaking during operation; and below the porous plug plate, a U-shaped sealing ring is arranged in an area enclosed by the confining pressure rubber bucket, the plug oil cylinder, and the plug piston assembly to prevent a porous medium from leaking into gaps.

Further, because a full-scale well casing has a large interface on the reactor cover, multiple functions can be expanded. The full-scale well casing is replaced with a piezocone test (CPTU) probe to calibrate penetration resistance and cone tip resistance characteristics of the reservoir after different degrees of $CO_2$ sequestration; or the full-scale well casing is replaced with a small drilling rig to study drilling characteristics of the reservoir after the $CO_2$ sequestration.

Further, the multi-physical field detection system further includes one or more of a pressure sensor measuring column, a temperature sensor measuring column, an acoustic dipole sensor, an electrical resistance tomography sensor, optical fiber sensors, or a confining pressure sensor; data acquisition cables of each sensor pass through the reactor cover and are connected to an external data acquisition system;

the pressure sensor measuring column and the temperature sensor measuring column are arranged in a "one hole with multiple pipes" and "one pipe with multiple lines" mode, i.e., measuring column holes are provided on the reactor cover, a sealing sleeve is inserted at each of the measuring column holes, a plurality of pressure or temperature sensor conduits are arranged inside the sealing sleeve, the plurality of pressure or temperature sensor conduits and the sealing sleeve are welded by silver welding to form the pressure sensor measuring column or the temperature sensor measuring column, and the pressure sensor measuring column and the temperature sensor measuring column are each tightly connected to the reactor cover with a clamping nut; and the temperature sensor measuring column requires filling of heat-conducting grease in the sealing sleeve to improve temperature measurement precision. The above design can greatly reduce the number of sensors arranged and reduce the artificial damage to the reservoir, and allows for convenient replacement of the measuring columns at any time in the closed state of the reactor.

The optical fiber sensors are distributed around the confining pressure rubber bucket and the full-scale well casing to monitor deformation of a reservoir and the well casing and characteristics of temperature-pressure-force evolution.

The acoustic dipole sensor is connected to symmetrically distributed acoustic dipoles arranged in the reservoir, to study an occurrence form and a distribution law of a fluid flow process according to changes of acoustic characteristics.

The confining pressure sensor is arranged on a pipeline connected between a confining pressure tracking pump and the confining pressure chamber to monitor a pressure change in the confining pressure chamber.

The electrical resistance tomography sensor is connected to a plurality of resistivity electrodes to implement electrical resistance tomography to obtain a three-dimensional spatial distribution and a migration law of the fluid in the reactor during the $CO_2$ geological sequestration and realize three-dimensional imaging of the migration law of the fluid in the high-pressure airtight reactor. Each of the plurality of resistivity electrodes is an integral structure including an electrode sheet and a stud. The stud is perpendicular to a center of the electrode sheet, a surface of the electrode sheet is an arc surface having a same curvature radius as an inner surface of the confining pressure rubber bucket, and the electrode sheet is embedded in a hole pre-formed on an inner wall of the confining pressure rubber bucket, to ensure that the inner surface of the confining pressure rubber bucket is smooth and flat, and avoid impacts of the electrode sheet on deformation and migration of sediments during the $CO_2$ geological sequestration. A concave-convex sealing R arc is provided at an unthreaded rod of the stud, and the unthreaded rod of the stud is inserted into the confining pressure rubber bucket by an interference fit and then tightly pressed by a washer and a nut to realize self-sealing and prevent internal deposits and fluids from leaking from the electrode sheet. A wiring nut is arranged on the stud to connect to a resistivity acquisition instrument.

Further, the reactor body is sealed by a self-tightening sealing structure, where a horizontal contact surface and a vertical contact surface between the reactor cover and the reactor body are respectively sealed by an O-shaped sealing ring group and a sealing ring. The self-tightening sealing structure is resistant to chemical media and gas corrosion, anti-extrusion, anti-gas explosion. After the reactor cover is aligned with the reactor body, the reactor cover can fit with the reactor body by a weight of the reactor cover. A 316 stainless steel anti-corrosion coating is formed on an inner wall of the reactor body by surfacing welding. An anti-corrosion kit is arranged at an opening on the reactor body and on the reactor cover, by drilling a large hole, embedding and welding a 316 stainless steel bar to the large hole, and then drilling a small hole, to prevent corrosion by acidic media such as seawater and $CO_2$ during an experiment. An outer side of the reactor body is connected to a reactor body overturning mechanism, and the reactor body is fixed at an arbitrary angle from 0 degrees to 180 degrees under control of a motor, to simulate conditions for a horizontal gravity field, a vertical gravity field, and gravity fields at different angles.

Further, the temperature control system includes a reactor body temperature control system connected to a circulating water jacket structure mounted on an outer wall of the reactor body to control the internal temperature of the high-pressure reactor; and the temperature control system further includes a stepping type low-temperature thermostatic chamber, where the reactor body is arranged in the stepping type low-temperature thermostatic chamber, and the ambient temperature of the high-pressure reactor is controlled by an air cooling system.

Further, the device further includes an auxiliary function system, where the auxiliary function system includes an industrial crane, a gas monitoring device, an explosion-proof ventilation device, an instrument electrical control cabinet, and a built-in model overturning mechanism, where the industrial crane is configured to transport and hoist a built-in model between the reactor body and the built-in model overturning mechanism; the gas monitoring device is configured to detect a gas concentration in an environment; the explosion-proof ventilation device is configured to provide ventilation for the environment; the instrument electrical control cabinet is configured to centrally control overall operation of the whole-process multi-parameter monitoring device for simulating the $CO_2$ geological sequestration; and the built-in model overturning mechanism is configured to realize disassembly or assembly of the built-in model outside the high-pressure reactor.

According to a second aspect of the present disclosure, a method for simulating $CO_2$ geological sequestration and monitoring changes of physical parameters in a reservoir with a progress of sequestration and stress loading in different directions using the whole-process multi-parameter monitoring device for simulating the $CO_2$ geological sequestration according to any one of the above embodiments is provided, including the following steps:

step 1: preparing the reservoir according to differences of physical parameters of natural reservoirs, where during the preparation of the reservoir, the acoustic dipoles are pre-buried in the reservoir at the same height as the plurality of resistivity electrodes, and the optical fiber sensors are pre-buried in the reservoir;

step 2: turning on the temperature control system and the fluid injection system, checking air tightness of the device, introducing nitrogen gas into the high-pressure reactor through the fluid injection system until an internal pressure of the high-pressure reactor reaches a target pressure; then closing valves on the high-pressure reactor, turning on the confining pressure tracking pump and the axial pressure tracking pump, restoring an in-situ stress condition of the reservoir, and controlling a pressure difference between an interior and an exterior of the confining pressure rubber bucket to be 1 MPa to 3 MPa to prevent the confining pressure rubber bucket from being damaged; observing a pressure change, where a pressure drop not greater than 0.01 MPa/h indicates that the device has good air tightness, and subsequent experiments are carried out;

step 3: releasing the nitrogen gas in the high-pressure reactor, introducing deionized water or multi-component salt solutions of different concentrations into the built-in model through the fluid injection system, and maintaining a pressure to ensure that pores in the reservoir are all filled with the deionized water; then introducing $CO_2$ gas into the built-in model at a constant rate through the fluid injection system until a target pressure is reached; at the same time, monitoring a change of a resistivity in the reservoir by using the electrical resistance tomography sensor and calculating a solubility of $CO_2$; obtaining changes of physical and chemical properties in the reservoir at an initial moment of the $CO_2$ sequestration; ensuring that temperatures inside and outside the high-pressure reactor each reach a target required temperature, monitoring a migration path and a distribution law of $CO_2$ in the high-pressure reactor in real time by using the electrical resistance tomography sensor, and monitoring mechanical changes at positions in the reservoir by using the optical fiber sensors, where the optical fiber sensors are at the same height as the resistivity electrodes, and the optical fiber sensors are configured to obtain in real time changes of mechanical properties of the reservoir with a $CO_2$ sequestration process; monitoring an axial deformation of the reservoir by using the axial pressure tracking pump; and step 4: adjusting a confining pressure in real time to prevent deformation of the confining pressure rubber bucket, where when a large amount of $CO_2$ is stored, pressure in the model drops at a high rate, and when the pressure drop in the reservoir is less than 0.05 MPa/12 h, the $CO_2$ sequestration is determined to be complete.

During the generation process, the changes of the electrical resistance tomography system, the optical fiber strain sensor system, and the acoustic dipole system are monitored in real time, the $CO_2$ distribution and migration behavior inside the model are monitored, and the evolution law of each phase component, gas-water-sand characteristics, reservoir deformation characteristics, and other important characteristics in the $CO_2$ sequestration process in the large-scale high-pressure system are obtained. Through the real reproduction of reservoir characteristics, modular built-in model and sample remodeling, in-situ real-time multi-dimensional monitoring of multi-physical field parameters, etc., the reservoir type, structural characteristics, boundary conditions, etc. are precisely controllable, and the experimental results obtained and numerical simulation results are mutually verifiable. The key reservoir characteristic parameters obtained by the system are easier to be expanded to the actual reservoir scale through a numerical simulation system, thereby effectively overcoming the shortcomings of conventional experimental systems in terms of scale, reservoir reproducibility, detection methods, and function scalability.

According to a third aspect of the present disclosure, a method for assembling the whole-process multi-parameter monitoring device for simulating $CO_2$ geological sequestration is provided, including the following steps:

step 1: arranging different types of injection wells and sensors on the reactor cover, arranging corresponding sensors around the confining pressure rubber bucket, checking whether the sensors at measuring points are firmly mounted or are missing, and measuring whether an insertion depth of each of the measuring points meets a requirement;

step 2: turning over the reactor cover so that a bottom of the reactor cover faces upward, mounting the confining pressure rubber bucket on the reactor cover in a manner of aligning the confining pressure rubber bucket with the reactor cover, filling the confining pressure rubber bucket with a porous medium layer by layer, and tamping the porous medium according to a target requirement;

step 3: after the filling is completed, arranging the temperature control system, part of components of the fluid injection system, and the plug assembly at an upper end of the confining pressure rubber bucket, and pre-tightening and fixing the reactor cover and the plug assembly to form a built-in model; turning over the built-in model by 180 degrees again so that a top of the reactor cover faces upward; and step 4: hoisting the built-in model into the reactor body, and closing and locking the snap ring, to complete assembly of a mock reactor.

The present disclosure has the following advantages. A whole-process multi-parameter monitoring device for simulating $CO_2$ geological sequestration is developed, which can restore the in-situ stress change of the real formation during the sequestration process, and at the same time, monitor in real time the changes of the electrical resistance tomography system and the optical fiber strain sensor system during the sequestration process, and monitor the distribution state of $CO_2$ in the model and the mechanical change characteristics of the reservoir during axial stress loading. The device can simultaneously monitor the changes of various parameters of "heat-pressure-sound-light-electricity" in real time during the sequestration process. The device can also obtain the characteristics of $CO_2$ sequestration in different geological environments, providing a theoretical basis for $CO_2$ sequestration in different regions. The device can solve a series of problems involved in simulation of the real sequestration process. The electrical resistance tomography and the optical fiber strain sensors are used to monitor the parameters inside the reservoir during the generation and sequestration process in real time and analyze reservoir characteristics.

DESCRIPTION OF THE EMBODIMENTS

Embodiments of the present disclosure will be described in further detail with reference to the accompanying drawings and examples. The following examples are intended to illustrate the present disclosure, instead of limiting the scope of the present disclosure.

Example 1

Figure 2:
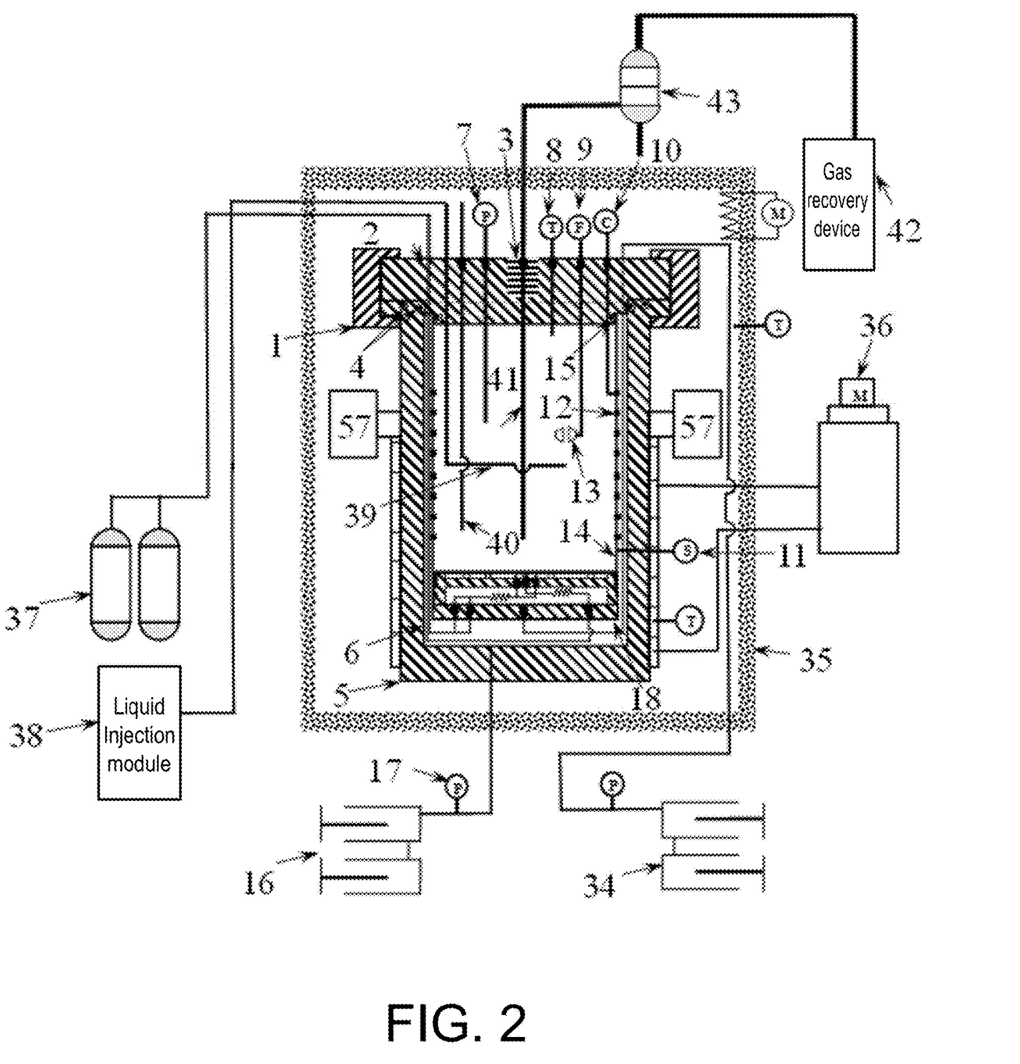
FIG. 2 is a schematic assembled view of the whole-process multi-parameter monitoring device for simulating $CO_2$ geological sequestration.

As shown in FIG. 2, a whole-process multi-parameter monitoring device for simulating $CO_2$ geological sequestration is provided, including a high-pressure reactor, a temperature control system, a fluid injection system, a mock sequestration system, and a multi-physical field detection system.

The temperature control system is configured to control an ambient temperature and an internal temperature of the high-pressure reactor. The temperature control system includes a reactor body temperature control system 36 connected to a circulating water jacket structure mounted on an outer wall of the reactor body 5 to control the internal temperature of the high-pressure reactor; and further includes a stepping type low-temperature thermostatic chamber 35. The reactor body 5 is arranged in the stepping type low-temperature thermostatic chamber 35. The ambient temperature of the entire reactor is controlled by an air cooling system.

The fluid injection system is configured to inject different types of fluids into the high-pressure reactor, to simulate the impact of different component environments on the efficiency of $CO_2$ sequestration.

The high-pressure reactor includes a reactor cover 2, a reactor body 5, a confining pressure rubber bucket 14, and a plug assembly 18. The reactor cover 2 is arranged above the reactor body 5. The reactor cover 2 is fixedly connected to an outer portion of the reactor body 5 by a snap ring 1. The confining pressure rubber bucket 14 is a bucket-shaped structure having an upper opening and a lower opening and is arranged inside the reactor body 5. An upper edge of the confining pressure rubber bucket 14 is sealedly connected to a lower end of the reactor cover 2, and a lower edge of the confining pressure rubber bucket 14 is sealedly connected to the plug assembly 18. The confining pressure rubber bucket 14 can adopt a modular installation scheme according to experimental requirements, and has a variety of shapes such as cylindrical shape, cube shape, and cylindrical shape with a fan-shaped cross section, to sealedly fit with corresponding bumps on the reactor cover respectively. A confining pressure chamber is formed between the confining pressure rubber bucket 14, the plug assembly 18, and the reactor body 5. The reactor body is a vessel structure having a single-layer thick-walled cylindrical body, and can withstand a pressure of 35 MPa, to simulate a reservoir at a water depth of 3500 meters. The reactor body 5 is made of high-strength alloy steel 20MnMoNbIV with a tensile strength of 530 σb/MPa to 700 σb/MPa and has a cavity size of φ800×1500 mm. The reactor body includes a refrigeration system having a refrigeration rate that can reduce the temperature of the high-pressure reactor from room temperature to −20° C. within 4 hours. The reactor is mounted vertically, and a bottom of the reactor can be connected with and supported by the base, so the reactor body and the cylindrical body form an integral structure.

The multi-physical field detection system includes different types of sensors arranged on the reactor cover 2, the reactor body 5, and the confining pressure rubber bucket 14 to implement multi-dimensional detection.

The device further includes an auxiliary function system, where the auxiliary function system includes an industrial crane 52, a gas monitoring device 53, an explosion-proof ventilation device 54, an instrument electrical control cabinet 55, and a built-in model overturning mechanism 56. The industrial crane 52 is configured to transport and hoist a built-in model between the reactor body 5 and the built-in model overturning mechanism 56. The gas monitoring device 53 is configured to detect a gas concentration in an environment. The explosion-proof ventilation device 54 is configured to provide ventilation for the environment. The instrument electrical control cabinet 55 is configured to centrally control overall operation of the whole-process multi-parameter monitoring device for simulating $CO_2$ geological sequestration. The built-in model overturning mechanism 56 is configured to realize disassembly or assembly of the built-in model outside the high-pressure reactor.

The reactor body is sealed by a self-tightening sealing structure. A horizontal contact surface and a vertical contact surface between the reactor cover 2 and the reactor body 5 are respectively sealed by an O-shaped sealing ring group 4 and a sealing ring 15. A 316 stainless steel anti-corrosion coating is formed on an inner wall 6 of the reactor body by surfacing welding. An anti-corrosion kit 3 is arranged at an opening on the reactor body and an opening on the reactor cover. An outer side of the reactor body 5 is connected to a reactor body overturning mechanism 57. The entire reactor body is fixed at an arbitrary angle from 0 degrees to 180 degrees under control of a motor, to simulate conditions for a horizontal gravity field, a vertical gravity field, and gravity fields at different angles.

Figure 3:
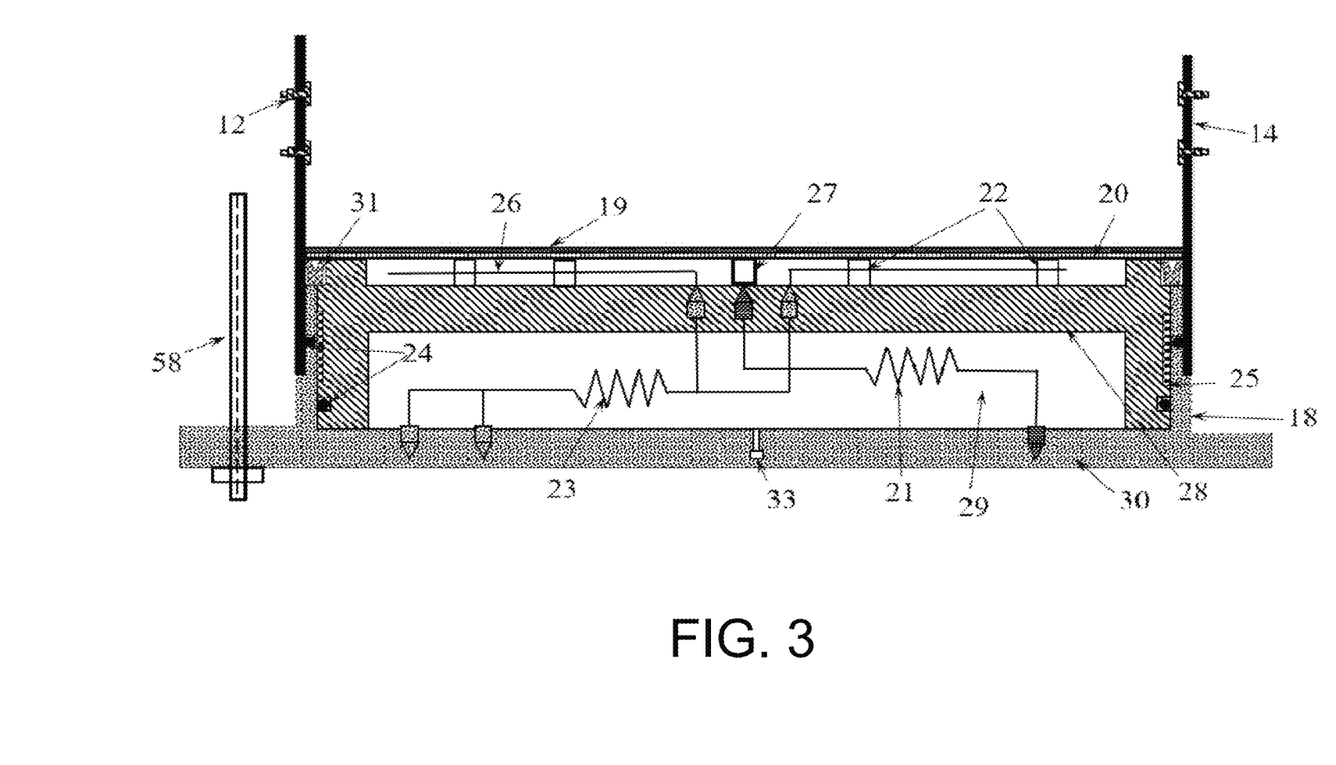
FIG. 3 is a schematic diagram of an axial stress loading device of the whole-process multi-parameter monitoring device for simulating $CO_2$ geological sequestration.

As shown in FIG. 3, the plug assembly 18 includes a plug cylinder 30 and a plug piston assembly 28. The lower edge of the confining pressure rubber bucket 14 is sleeved on and sealedly connected to an outer periphery of the plug cylinder 30. The plug piston assembly 28 is arranged in an upper portion of the plug cylinder 30, an outer wall of the plug piston assembly 28 is in close contact with and sealedly connected to an inner wall of the plug cylinder 30, and a hydraulic oil cavity 29 for accommodating a hydraulic oil is formed between a lower portion of the plug piston assembly 28 and the plug cylinder 30. A piston hydraulic interface 33 is arranged at a bottom of the plug cylinder 30, and axial stress loading is controlled by an axial pressure tracking pump 34. The plug piston assembly 28 is provided with a channel in communication with the fluid injection system, and the channel is configured to inject a fluid required for simulating $CO_2$ geological sequestration to the confining pressure rubber bucket 14.

Figure 4:
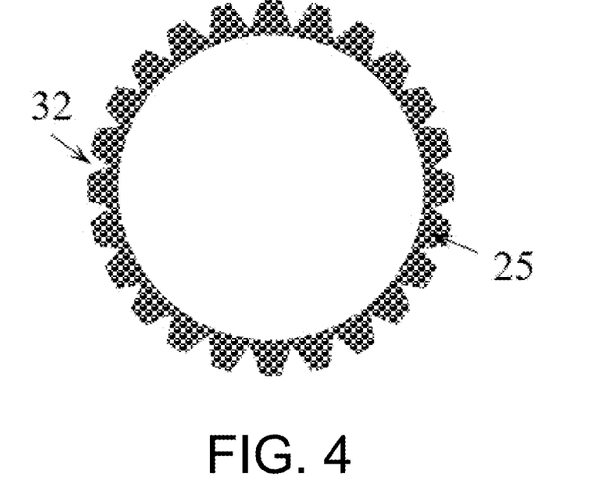
FIG. 4 is a schematic structural diagram of a copper sleeve wear-resistant ring.

A cavity is provided above the plug piston assembly 28. A porous plug plate 20 and a filter plate 19 covering a bottom section of the confining pressure rubber bucket 14 are arranged above the cavity in sequence from bottom to top. Holes are uniformly formed on the porous plug plate, and gas is injected into the confining pressure rubber bucket through the gas injection column 27 to prevent the porous medium from leaking out of the porous plug plate 20. A stainless steel sintered filter plate 19 is mounted on the porous plug plate. A heating circulation pipe 26 is arranged in the cavity to simulate a ground temperature gradient and form an underlying gas space. The ground temperature gradient is controlled in similar to the control of a vertical temperature gradient, where a maximum temperature difference is 5° C., and temperature control precision is ±0.5° C. The device can also be used to carry out a ground temperature gradient simulation experiment, and a temperature-controlled heating coil is additionally mounted on the top of the built-in model system or a temperature-controlled heating coil is pre-buried in the middle of the physical model during the sand filling operation, to realize a three-layer temperature control mode for the upper, middle, and lower layers. A supporting column 22 is arranged between a bottom of the cavity and the porous plug plate 20 to prevent a sand-filled sample from damaging the heating circulation pipe. The plug assembly 18 further includes a copper sleeve wear-resistant ring 25. The copper sleeve wear-resistant ring 25 is sheathed in a groove on an outer wall surface of the plug piston assembly 28. As shown in FIG. 4, a guide groove 32 is provided on an outer periphery of the copper sleeve wear-resistant ring 25 to prevent the plug piston assembly 28 from deviating during movement relative to the plug cylinder 30.

A gas injection column 27 is arranged in the cavity above the plug piston assembly 28. A gas injection transfer pipe 21 is arranged in a cavity below the plug piston assembly 28. A first end of the gas injection transfer pipe 21 is connected to the gas injection column 27, and a second end of the gas injection transfer pipe 21 is connected to a gas injection module 37 in the fluid injection system for injecting gas into a reservoir. A heat injection circulation transfer pipe 23 is further arranged in the cavity below the plug piston assembly 28. A first end of the heat injection circulation transfer pipe 23 is connected to the heating circulation pipe 26, and a second end of the heat injection circulation transfer pipe 23 is connected to a temperature control water bath. The heat injection circulation transfer pipe 23 is configured to simulate the ground temperature gradient and control a vertical temperature gradient. Both the gas injection transfer pipe 21 and the heat injection circulation transfer pipe 23 are spirally shaped to prevent damage to pipelines during displacement.

It can be seen that the plug assembly 18 has two main functions: formation temperature gradient simulation and axial stress loading.

The plug cylinder 30 is sealedly connected to the plug piston assembly 28 by a piston seal assembly 24, and the lower edge of the confining pressure rubber bucket 14 is sealedly connected to the outer periphery of the plug cylinder 30 by the piston seal assembly 24. A first end of a pre-tightening pull rod 58 is mounted on the plug cylinder 30 and a second end of the pre-tightening pull rod 58 is connected to the reactor cover 2 to prevent components from falling when the built-in model is taken out from the built-in model overturning mechanism 56. The built-in model mainly includes the reactor cover 2, the confining pressure rubber bucket 14, and the plug assembly 18. The piston seal assembly 24 is in the form of a combination of two support rings and an O-shaped sealing ring, and is configured to prevent the hydraulic oil in the hydraulic oil cylinder from leaking during operation. Below the porous plug plate 20, a U-shaped sealing ring 31 is arranged in an area enclosed by the confining pressure rubber bucket 14, the plug oil cylinder 30, and the plug piston assembly 28 to prevent sand particles from leaking into gaps. Particles in the groove receiving the U-shaped sealing ring 31 are cleaned periodically.

To prevent the confining pressure rubber bucket 14 from being deformed during the process of injecting gas into an interior of the built-in model, a confining pressure should be applied before the gas injection, and the pressure of the applied confining pressure should be 1 MPa to 3 MPa higher than the pressure of the gas injection. During the injection, the confining pressure is adjusted using the confining pressure tracking pump 16.

The axial loading pressure is determined by a pressure difference between a hydraulic loading pressure and an experimental pressure inside the built-in model. Axial stress loading indicators:

Axial loading pressure difference indicator:
$\Delta P_{axis} = P_{hydraulic} - P_{experiment}$
Axial loading thrust indicator:

$$F_{axis} = \frac{\pi D^2}{4}(P_{hydraulic} - P_{experiment})$$

In the formula, F is measured in N, P is measured in MPa, and D is measured in mm.

In an example of calculating the axial stress loading indicators, it is assumed that the maximum pressure in the built-in model is 30 MPa, and $P_{hydraulic}=31$ MPa. As calculated according to the above formula, the axial pressure is about 301907 N, i.e., about 30806 Kgf. The built-in model is filled with quartz sand with a density of approximately 2.5 g/cm³ and a weight of 995 Kg. The maximum weight of pore water is 393 Kg. The maximum weight in the built-in model is 1388 Kg, which is far less than a thrust generated by the pressure difference of 1 MPa, so axial stress loading can be realized.

Figure 1:
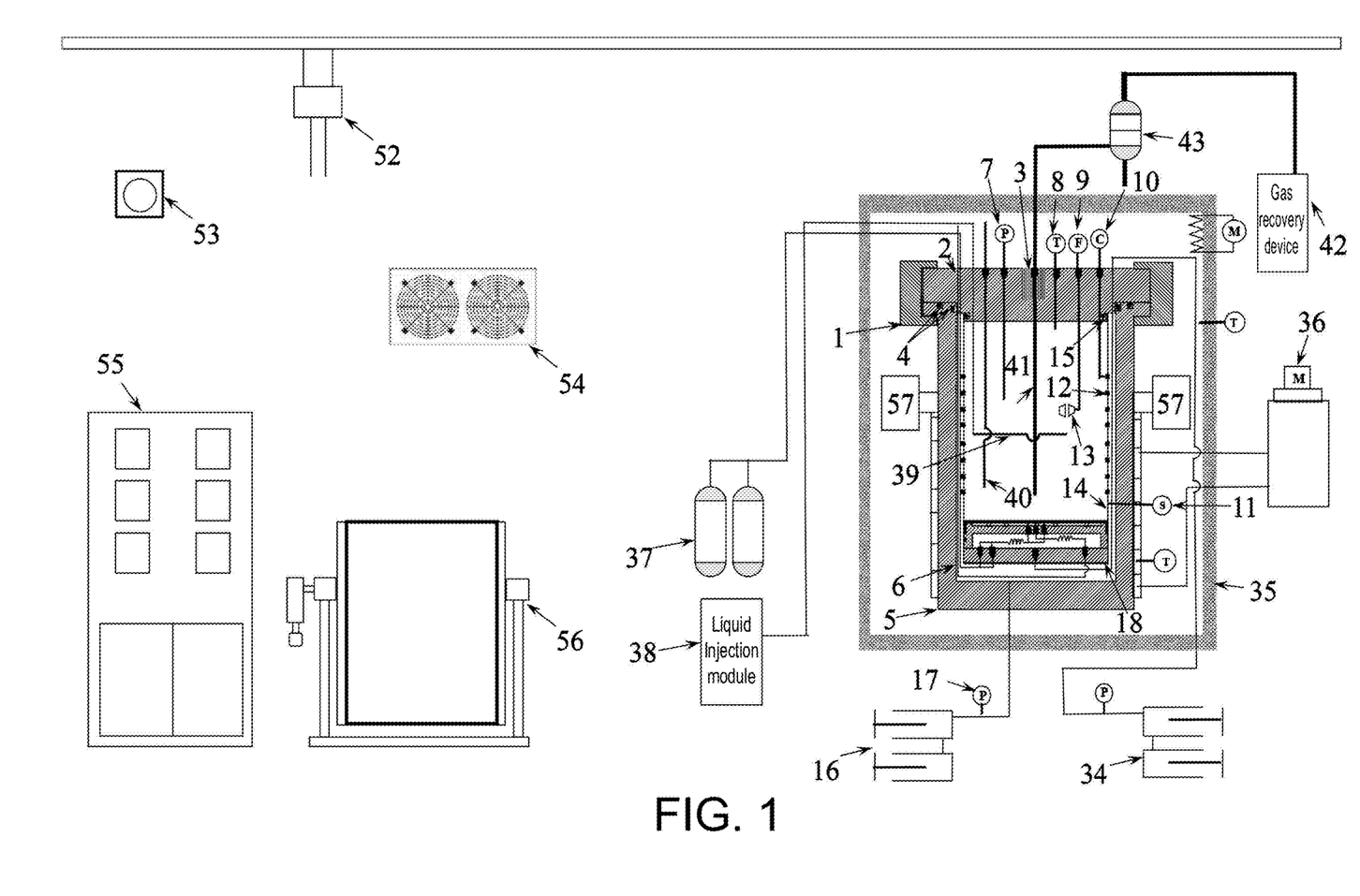
FIG. 1 is a schematic structural diagram of a whole-process multi-parameter monitoring device for simulating $CO_2$ geological sequestration.

The multi-physical field detection system includes one or more of a pressure sensor measuring column 7, a temperature sensor measuring column 8, an acoustic dipole sensor 9, an electrical resistance tomography sensor 10, optical fiber sensors 11, or a confining pressure sensor 17. Data acquisition cables of the sensors pass through the reactor cover 2 and are connected to an external data acquisition system.

Measuring column holes are provided on the reactor cover 2. A sealing sleeve is inserted at each of the measuring column holes. A plurality of pressure or temperature sensor conduits are arranged inside each of the sealing sleeves. The conduits and the sealing sleeve are welded by silver welding to form the pressure sensor measuring column 7 or the temperature sensor measuring column 8. The measuring columns are tightly connected to the reactor cover with a clamping nut. The temperature sensor measuring column 8 requires filling of heat-conducting grease in the sealing sleeve to improve temperature measurement precision.

The pressure sensor measuring column 7 is arranged longitudinally and vertically extending into a deposition layer, and is in the form of a measuring tube-type assembly, which is inserted into three positions in the model, namely, positions which are respectively 300 mm, 600 mm, and 900 mm away from an inner top wall of the model. The pressure sensor measuring column is designed as a "three-pipe-in-one-hole" assembly. Three pressure conduits are inserted into the sealing sleeve. A head of each pressure conduit is wrapped with a screen and fixed by threads. The pressure measuring column is tightly coupled to the reactor cover by a M27×2 clamping nut.

The temperature sensor measuring column 8 is in the form of an integrated suit, including four PT100A temperature sensors mounted in a 316 stainless steel φ10 mm steel pipe according to different heights to measure the temperature at different positions in the built-in model. Before the temperature sensors are inserted into the suit pipe, a heat conductive oil or heat conductive grease is introduced into the suit pipe, so that the temperature value inside the reservoir can be more precisely measured. The temperature sensors in the suit pipe are inserted into four positions of the model, namely, positions which are respectively 150 mm, 450 mm, 750 mm, and 1050 mm away from the top of the physical model. In this example, a total of 12 temperature measuring columns are mounted, and a total of 12×4=48 channels of temperature data are provided. The temperature measuring columns are arranged in a matrix at intervals of 200 mm with an axis of the flat-top reactor cover as the center. A heat source insulation coating is sprayed on a surface of the suit pipe, and surface roughening treatment is carried out, to prevent gas and liquid from flowing along the wall to cause heat loss. The insulation coating on the surface reduces the impact of metals on electrical resistivity imaging.

Figure 5:
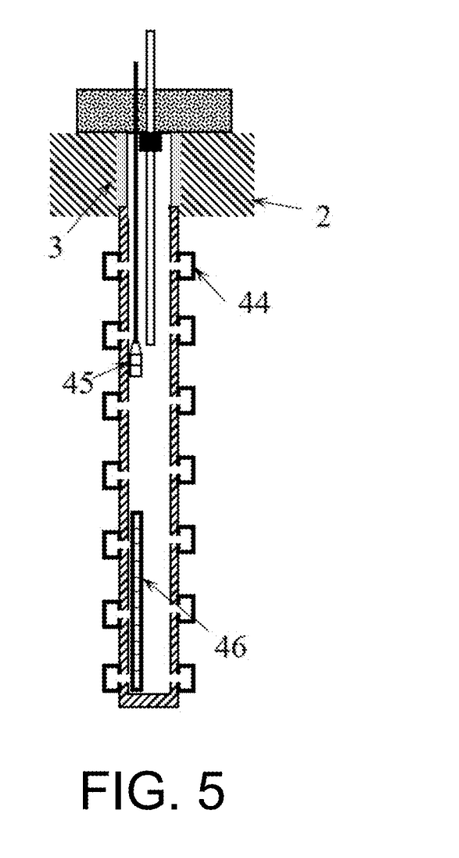
FIG. 5 is a schematic structural enlarged view of a full-scale well casing.

The optical fiber sensors 11 are distributed around the confining pressure rubber bucket 14 and a full-scale well casing 41 to monitor deformation of the reservoir and the well casing. The optical fiber sensors 11 are configured to monitor the deformation of the reservoir and the full-scale well casing 41 during the $CO_2$ generation process. During the preparation of the reservoir, the optical fiber sensors are arranged inside the reservoir and on the full-scale well casing 41 to monitor in real time the stresses inside the reservoir and on the full-scale well casing during sequestration. The hydraulic oil is injected into the hydraulic oil cylinder while simulating $CO_2$ geological sequestration. The plug piston assembly 28 is configured to displace along the guide groove 32 under the action of the pressure difference, to form an axial pressure in the built-in model system. The deformation inside the reservoir and the deformation of the full-scale well casing 41 are detected using the optical fiber sensors 11. The resistivity electrodes 12 are configured to monitor a degree of $CO_2$ sequestration.

The acoustic dipole sensor 9 is connected to symmetrically distributed acoustic dipoles 13 arranged in the reservoir, to study an occurrence form and a distribution law of a fluid flow process according to changes of acoustic characteristics.

The confining pressure sensor 17 is arranged on a pipeline connected between the confining pressure tracking pump 16 and the confining pressure chamber to monitor a pressure change in the confining pressure chamber.

Figure 6:
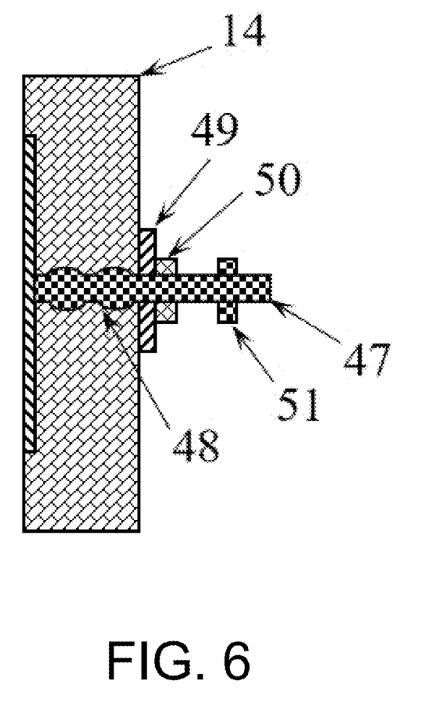
FIG. 6 is a schematic structural enlarged view of an electrical resistance tomography sensor.

The electrical resistance tomography sensor 10 is connected to the plurality of resistivity electrodes 12 to implement electrical resistance tomography. Each of the resistivity electrodes 12 is an integral structure including an electrode sheet and a stud 47. The stud is perpendicular to a center of the electrode sheet. A surface of the electrode sheet is an arc surface having the same curvature radius as an inner surface of the confining pressure rubber bucket 14. The electrode sheet is embedded in a hole pre-formed on an inner wall of the confining pressure rubber bucket 14, to ensure that the inner surface of the confining pressure rubber bucket 14 is smooth and flat, and avoid impacts of the electrode sheet on deformation and migration of sediments during sequestration. The electrodes are directly in close contact with the reservoir in the rubber bucket to avoid the flow of electrical signals around the high-pressure metal reactor. A concave-convex sealing R arc 48 is provided at an unthreaded rod of the stud. The unthreaded rod of the stud is inserted into the confining pressure rubber bucket 14 by an interference fit and then tightly pressed by a washer 49 and a nut 50 to realize self-sealing and prevent internal deposits and fluids from leaking from the electrode sheet. A wiring nut 51 is arranged on the stud to connect to a resistivity acquisition instrument. Eight layers are arranged in the vertical direction of the rubber bucket, and 16 electrodes are arranged in each layer. The size of the electrode plate may be adjusted according to a resistance of the medium under test. During the measurement, a fixed current is injected into one electrode, and electrical signals between the electrode and the other 15 electrodes are obtained. The measurement is carried out along the cyclic sequence. 120 pieces of slice data can be obtained for each layer, and a total of 960 pieces of slice data are obtained for the eight layers. Through basic resistivity calibration of dry core, saturated brine core, and core with different water contents, etc., a resistivity data analysis and inversion algorithm are formed, a three-dimensional spatial distribution and migration law of the fluid in the reactor during $CO_2$ geological sequestration are obtained, and three-dimensional imaging of the migration law of the fluid in the high-pressure airtight reactor is realized.

The mock sequestration system includes a vertical well 40, a horizontal well 39, and the full-scale well casing 41. The full-scale well casing 41 is arranged in the middle of the reactor cover 2, and the full-scale well casing 41 includes a full-scale well, and one or more of a high-pressure endoscopic imaging system 45, a grit height detection system 46, and the heating circulation pipe. Well holes 44 are formed on a wall of the full-scale well casing. A drainage hole is formed below the full-scale well casing to discharge excess water in the full-scale well casing. A stainless steel screen is wrapped at the drainage hole to prevent sand in the drained water from damaging pipe and valve parts during drainage. A damping coil is further mounted at the drainage hole to stabilize a high-pressure water flow discharged from the high-pressure reactor to avoid jetting. The heating circulation pipe is arranged in the full-scale well casing to prevent formation of a hydrate in a well bore during simulation of low-temperature high-pressure $CO_2$ sequestration resulting in impacts on illumination and observation in the well bore. The high-pressure endoscopic imaging system 45 is arranged in the full-scale well casing to observe the fluid flowing into the well casing through the porous medium. The grit height detection system 46 is arranged at a bottom of the full-scale well casing to monitor accumulation of the porous medium in the full-scale well casing. In the reactor body 5, the vertical well 40 is arranged perpendicularly to a wall surface of the reactor cover 2, and the horizontal well 39 is arranged perpendicularly to a wall surface of the reactor body 5. The vertical well 40 and the horizontal well 39 are connected to a liquid injection module 38 through external pipes. During preparation of the reservoir, the optical fiber sensors 11 are arranged around the full-scale well casing 41 to monitor well casing deformation. In the mock sequestration system, a three-phase separator 43 and a gas recovery device 42 are mounted at an outlet of generated gas to treat tail gas.

With the horizontal well 39 and the vertical well 40, multi-well simulation involving the vertical well and the horizontal well can be carried out. Simulation of inverted five-spot, seven-spot, and nine-spot multi-well injection modes for $CO_2$ and different fluids is achieved. Four layers having the same height of 300 mm are preferably selected from the built-in physical model. The vertical well pattern is arranged in a square shape, and mounted on the flat-top cover of the high-pressure reactor connected to the built-in physical model. There are a total of 9 groups of vertical wells extending deep into the model. The horizontal well pattern is arranged in a square shape.

The fluid injection system includes a gas injection module 37 and a liquid injection module 38. The gas injection module mainly includes a gas source cylinder group, an air compressor, a booster pump, a high-pressure buffer tank, a pressure regulator, a gas filter, a gas flowmeter, a pipeline, etc. The gas injection module can provide $CO_2$ at a stable pressure and flow rate to the built-in model of the reactor, and quantitatively inject a replacement gas such as $CO_2$ at a stable pressure and flow rate into the reactor during replacement. The liquid injection module 38 mainly includes a liquid container, an electronic scale, a high-pressure injection pump, a heating container, a pressure gauge, a pressure sensor, a temperature sensor, a safety valve, a filter, a stop valve, a pipeline, etc., and is configured to quantitatively inject a liquid into the built-in model of the reactor to meet different fluid injection requirements.

The full-scale well casing is replaced with a CPTU probe to calibrate penetration resistance and cone tip resistance characteristics of the reservoir after sequestration. Alternatively, the full-scale well casing is replaced with a small drilling rig to study drilling characteristics of the reservoir after $CO_2$ sequestration.

Example 2

Use of the whole-process multi-parameter monitoring device for simulating $CO_2$ geological sequestration in simulating $CO_2$ geological sequestration and monitoring changes of physical parameters in a reservoir with a progress of sequestration and stress loading in different directions is provided, including the following steps.

In step 1, a reservoir is prepared according to differences of physical parameters of natural reservoirs. During the preparation of the reservoirs, the acoustic dipoles are pre-buried in the reservoir at the same height as the resistivity electrodes, and the optical fiber sensors are arranged on the full-scale well casing.

In step 2, the temperature control system and the fluid injection system are turned on, air tightness of the entire device is checked, nitrogen gas is introduced into the high-pressure reactor through the fluid injection system until an internal pressure of the high-pressure reactor reaches a target pressure; then, valves on the high-pressure reactor are closed, the confining pressure tracking pump and the axial pressure tracking pump are turned on, an in-situ stress condition of the reservoir is restored, and a pressure difference between an interior and an exterior of the confining pressure rubber bucket 14 is controlled to be 1 MPa to 3 MPa to prevent the confining pressure rubber bucket 14 from being damaged; a pressure change is observed, where a pressure drop not greater than 0.01 MPa/h indicates that the device has good air tightness, and subsequent experiments are carried out.

In step 3, the nitrogen gas in the high-pressure reactor is released, deionized water or multi-component salt solutions of different concentrations are introduced into the built-in model system through the fluid injection system, and the pressure is maintained to ensure that pores in the reservoir are all filled with deionized water; then $CO_2$ gas is introduced into the built-in model system at a constant rate through the fluid injection system until a target pressure is reached; at the same time, a change of a resistivity in the reservoir is monitored by using the electrical resistance tomography sensor 10 and a solubility of $CO_2$ is calculated; initial physical and chemical properties of the reservoir are obtained; it is ensured that temperatures inside and outside the high-pressure reactor reach a target required temperature, a three-dimensional distribution state of $CO_2$ in the reactor is monitored in real time by using the electrical resistance tomography sensor 10, and mechanical changes at positions in the reservoir are monitored by using the optical fiber sensors 11, where the optical fiber sensors are at the same height as the resistivity electrodes, and are configured to obtain in real time changes of mechanical properties of the reservoir with the sequestration process; and an axial deformation of the reservoir is monitored by using the axial pressure tracking pump 34.

In step 4, a confining pressure is adjusted in real time to prevent deformation of the confining pressure rubber bucket 14. When a large amount of $CO_2$ is stored, pressure in the model drops at a high rate, and when the pressure drop in the reservoir is less than 0.05 MPa/12 h, the $CO_2$ sequestration is determined to be complete.

During the generation process, the changes of the electrical resistance tomography system, the optical fiber strain sensor system, and the acoustic dipole system are monitored in real time, the amount of $CO_2$ stored inside the model and the mechanical change characteristics of the reservoir during axial stress loading are monitored, and the evolution law of each phase component, gas-water-sand characteristics, reservoir deformation characteristics, and other important characteristics in the $CO_2$ sequestration process in the large-scale reaction system are obtained. Through the real reproduction of reservoir characteristics, modular built-in model and sample remodeling, in-situ real-time multi-dimensional monitoring of multi-physical field parameters, etc., the reservoir type, structural characteristics, boundary conditions, etc. are precisely controllable and are kept consistent with those in a numerical simulation system, and the experimental results obtained and numerical simulation results are mutually verifiable. The key reservoir characteristic parameters obtained by the system are easier to be expanded to the actual reservoir scale through the numerical simulation system, thereby effectively overcoming the shortcomings of conventional experimental systems in terms of scale, reservoir reproducibility, detection methods, and function scalability.

Example 3

A method for assembling the whole-process multi-parameter monitoring device for simulating $CO_2$ geological sequestration is provided, including the following steps.

In step 1, different types of injection wells and sensors are arranged on the reactor cover 2, corresponding sensors are arranged around the confining pressure rubber bucket 14, it is checked whether a sensor at each measuring point is firmly mounted or is missing, and it is measured whether an insertion depth of each measuring point meets a requirement. Resistivity measuring points are fixed on the confining pressure rubber bucket 14 through studs 47 or other accessories. There are a total of 128 measuring points placed for later use.

In step 2, after the mounting of the reactor cover 2 is checked to be qualified, the built-in model overturning mechanism 56 is rotated by 180° so that the reactor cover 2 faces downward, and a safety positioning pin is locked. The confining pressure rubber bucket 14 is hoisted, aligned with and mounted on the reactor cover. The confining pressure rubber bucket is filled with a porous medium layer by layer, and the porous medium is tamped according to an experimental requirement. During the filling process, according to design requirements, horizontal wells 39 are sequentially inserted through horizontal well holes reserved in the rubber bucket, with three horizontal wells in each layer. Exposed ends of the horizontal wells are connected to a snap joint and led out to an outer part of the reactor cover. In addition, the acoustic dipole sensor 9 is pre-buried according to a design height.

In step 3, after the filling is completed, the temperature control system, part of components of the fluid injection system, and the plug assembly 18 are arranged at an upper end of the confining pressure rubber bucket 14. The stainless steel sintered filter plate 19, the porous plug plate 20, and the plug assembly 18 are sequentially mounted. An optical fiber strain sensor is mounted on a periphery of the confining pressure rubber bucket 14, and is connected to a high-pressure multi-core watertight connector and thus led out of the reactor cover. The reactor cover 2 and the plug assembly 18 are connected by 16 pre-tightening pull rods 58, and are thus pre-tightened and fixed to form a built-in model. Signal lead-out lines of various sensors, gas injection pipelines, and the heating circulation pipe for ground temperature simulation are connected to the outside of the reactor through the flat-top reactor cover 2. The positioning pin is removed, the built-in model is turned over by 180 degrees again so that the top of the reactor cover 2 faces upward, and then the positioning pin is inserted back. It is checked whether each signal line and gas/liquid pipeline is firmly connected or is not connected, and the pressure is tested for leakage detection to prepare for hoisting.

In step 4, the snap ring 1 of the reactor cover is opened to the maximum degree, the industrial crane 52 is turned on, and the built-in model of the reactor is assembled in the reactor. The snap ring is closed and locked with a bolt. Thus, the assembly of the mock reactor is completed. Well casings, pressure sensors, acoustic dipoles, temperature sensor signal lines, etc. outside the high-pressure reactor are connected to proceed to the next experimental stage.

The embodiments of the present disclosure are presented for purposes of illustration and description, and are not intended to be exhaustive or to limit the present disclosure to the form disclosed. Various modifications and variations are obvious to those of ordinary skill in the art. The embodiments are chosen and described in order to well explain the principles of the present disclosure and the practical application, and to enable those of ordinary skill in the art to understand the present disclosure and design various embodiments with various modifications as are suited to the particular use contemplated.

What is claimed is:
1. A whole-process multi-parameter monitoring device for simulating $CO_2$ geological sequestration, comprising a high- pressure reactor, a temperature control system, a fluid injection system, and a multi-physical field detection system, wherein the temperature control system is configured to control an ambient temperature and an internal temperature of the high-pressure reactor;

the fluid injection system is configured to inject different types of fluids into the high-pressure reactor;

the high-pressure reactor comprises a reactor cover, a reactor body, a confining pressure rubber bucket, and a plug assembly; the reactor cover is arranged above the reactor body, and the reactor cover is fixedly connected to an outer portion of the reactor body by a snap ring; the confining pressure rubber bucket is a bucket-shaped structure having an upper opening and a lower opening and is arranged inside the reactor body, an upper edge of the confining pressure rubber bucket is sealedly connected to a lower end of the reactor cover, and a lower edge of the confining pressure rubber bucket is sealedly connected to the plug assembly; a confining pressure chamber is formed by the confining pressure rubber bucket, the plug assembly, and the reactor body; the plug assembly comprises a plug cylinder and a plug piston assembly; the lower edge of the confining pressure rubber bucket is sleeved on and sealedly connected to an outer periphery of the plug cylinder; the plug piston assembly is arranged in an upper portion of the plug cylinder, an outer wall of the plug piston assembly is in close contact with and sealedly connected to an inner wall of the plug cylinder, and a hydraulic oil cavity for accommodating a hydraulic oil is formed between a lower portion of the plug piston assembly and the plug cylinder; a piston hydraulic interface is arranged at a bottom of the plug cylinder, and axial stress loading is controlled by an axial pressure tracking pump; the plug piston assembly is provided with a channel in communication with the fluid injection system, and the channel is configured to inject a fluid required for simulating the $CO_2$ geological sequestration to the confining pressure rubber bucket;

the multi-physical field detection system comprises different types of sensors arranged on the reactor cover, the reactor body, and the confining pressure rubber bucket to implement multi-dimensional detection; and the sensors comprise an electrical resistance tomography sensor connected to a plurality of resistivity electrodes on the confining pressure rubber bucket to implement electrical resistance tomography, a cavity is provided above the plug piston assembly, and a porous plug plate and a filter plate covering a bottom section of the confining pressure rubber bucket are arranged above the cavity in sequence from bottom to top, the cavity above the plug piston assembly is defined between an upper portion of the plug piston assembly and the porous plug plate, and a gas injection column is arranged in the cavity above the plug piston assembly, the hydraulic oil cavity is provided below the plug piston assembly, a gas injection transfer pipe is arranged in the hydraulic oil cavity below the plug piston assembly, and a first end of the gas injection transfer pipe is connected to the gas injection column, the porous plug plate is provided with holes uniformly drilled thereon, and is configured to support a porous medium; a pore size of the filter plate prevents the porous medium from leaking out of the porous plug plate; a heating circulation pipe is arranged in the cavity above the plug piston assembly to control a ground temperature gradient; and a supporting column is arranged between a bottom of the cavity above the plug piston assembly and the porous plug plate to prevent a sand-filled sample from damaging the heating circulation pipe.

2. The whole-process multi-parameter monitoring device for simulating the $CO_2$ geological sequestration according to claim 1, wherein the plug assembly further comprises a copper sleeve wear-resistant ring, the copper sleeve wear-resistant ring is sheathed in a groove on an outer wall surface of the plug piston assembly, and a guide groove is provided on an outer periphery of the copper sleeve wear-resistant ring to prevent the plug piston assembly from deviating during movement relative to the plug cylinder.

3. The whole-process multi-parameter monitoring device for simulating the $CO_2$ geological sequestration according to claim 1, wherein a second end of the gas injection transfer pipe is connected to a gas injection module in the fluid injection system for injecting gas into a reservoir; a heat injection circulation transfer pipe is further arranged in the hydraulic oil cavity below the plug piston assembly, a first end of the heat injection circulation transfer pipe is connected to the heating circulation pipe, a second end of the heat injection circulation transfer pipe is connected to a temperature control water bath, and the heat injection circulation transfer pipe is configured to simulate the ground temperature gradient and control a vertical temperature gradient; and both the gas injection transfer pipe and the heat injection circulation transfer pipe are spirally shaped to prevent damage to pipelines during displacement.

4. The whole-process multi-parameter monitoring device for simulating the $CO_2$ geological sequestration according to claim 1, wherein the multi-physical field detection system further comprises one or more of a pressure sensor measuring column, a temperature sensor measuring column, an acoustic dipole sensor, optical fiber sensors, or a confining pressure sensor; data acquisition cables of each sensor pass through the reactor cover and are connected to an external data acquisition system;

measuring column holes are provided on the reactor cover, a sealing sleeve is inserted at each of the measuring column holes, a plurality of pressure or temperature sensor conduits are arranged inside the sealing sleeve, the plurality of pressure or temperature sensor conduits and the sealing sleeve are welded by silver welding to form the pressure sensor measuring column or the temperature sensor measuring column, and the pressure sensor measuring column or the temperature sensor measuring column are each tightly connected to the reactor cover with a clamping nut; the temperature sensor measuring column requires filling of heat-conducting grease in the sealing sleeve to improve temperature measurement precision;

the optical fiber sensors are distributed around the confining pressure rubber bucket to monitor deformation of a reservoir;

the acoustic dipole sensor is connected to symmetrically distributed acoustic dipoles arranged in the reservoir, to study an occurrence form and a distribution law of a fluid flow process according to changes of acoustic characteristics;

the confining pressure sensor is arranged on a pipeline connected between a confining pressure tracking pump and the confining pressure chamber to monitor a pressure change in the confining pressure chamber;

the electrical resistance tomography sensor is connected to the plurality of resistivity electrodes to implement the electrical resistance tomography; each of the plurality of resistivity electrodes is an integral structure comprising an electrode sheet and a stud, the stud is perpendicular to a center of the electrode sheet, a surface of the electrode sheet is an arc surface having a same curvature radius as an inner surface of the confining pressure rubber bucket, and the electrode sheet is embedded in a groove pre-formed on an inner wall of the confining pressure rubber bucket, to ensure that the inner surface of the confining pressure rubber bucket is smooth and flat, and avoid impacts of the electrode sheet on deformation and migration of sediments during the $CO_2$ geological sequestration; a concave-convex sealing radius arc is provided at an unthreaded rod of the stud, and the unthreaded rod of the stud is inserted into the confining pressure rubber bucket by an interference fit and then tightly pressed by a washer and a nut to realize self-sealing and prevent internal deposits and fluids from leaking from the electrode sheet; and a wiring nut is arranged on the stud to connect to a resistivity acquisition instrument.

5. The whole-process multi-parameter monitoring device for simulating the $CO_2$ geological sequestration according to claim 1, wherein the reactor body is sealed by a self-tightening sealing structure, a horizontal contact surface and a vertical contact surface between the reactor cover and the reactor body are respectively sealed by an O-shaped sealing ring group and a sealing ring; a 316 stainless steel anti-corrosion coating is formed on an inner wall of the reactor body by surfacing welding; an anti-corrosion kit is arranged at an opening on the reactor body and on the reactor cover; and an outer side of the reactor body is connected to a reactor body overturning mechanism, and the reactor body is fixed at an arbitrary angle from 0 degrees to 180 degrees under control of a motor, to simulate conditions for a horizontal gravity field, a vertical gravity field, and gravity fields at different angles.

6. The whole-process multi-parameter monitoring device for simulating the $CO_2$ geological sequestration according to claim 1, wherein the temperature control system comprises a reactor body temperature control system connected to a circulating water jacket structure mounted on an outer wall of the reactor body to control the internal temperature of the high-pressure reactor; and the temperature control system further comprises a stepping type low-temperature thermostatic chamber, wherein the reactor body is arranged in the stepping type low-temperature thermostatic chamber, and the ambient temperature of the high-pressure reactor is controlled by an air cooling system.

7. The whole-process multi-parameter monitoring device for simulating the $CO_2$ geological sequestration according to claim 1, further comprising an auxiliary function system, wherein the auxiliary function system comprises an industrial crane, a gas monitoring device, an explosion-proof ventilation device, an instrument electrical control cabinet, and a built-in model overturning mechanism, wherein the industrial crane is configured to transport and hoist a built-in model between the reactor body and the built-in model overturning mechanism; the gas monitoring device is configured to detect a gas concentration in an environment; the explosion-proof ventilation device is configured to provide ventilation for the environment; the instrument electrical control cabinet is configured to centrally control overall operation of the whole-process multi-parameter monitoring device for simulating the $CO_2$ geological sequestration; and the built-in model overturning mechanism is configured to realize disassembly or assembly of the built-in model outside the high-pressure reactor.

8. The whole-process multi-parameter monitoring device for simulating the $CO_2$ geological sequestration according to claim 1, wherein the plug cylinder is sealedly connected to the plug piston assembly by a piston seal assembly, and the lower edge of the confining pressure rubber bucket is sealedly connected to the outer periphery of the plug cylinder by the piston seal assembly; a first end of a pre-tightening pull rod is mounted on the plug cylinder and a second end of the pre-tightening pull rod is connected to the reactor cover to prevent components from falling when the built-in model is taken out from the built-in model overturning mechanism, and the built-in model mainly comprises the reactor cover, the confining pressure rubber bucket, and the plug assembly; the piston seal assembly is in a form of a combination of two support rings and an O-shaped sealing ring, and is configured to prevent the hydraulic oil in a hydraulic oil cylinder from leaking during operation; and below the porous plug plate, a U-shaped sealing ring is arranged in an area enclosed by the confining pressure rubber bucket, the plug oil cylinder, and the plug piston assembly to prevent a porous medium from leaking into gaps.

9. The whole-process multi-parameter monitoring device for simulating the $CO_2$ geological sequestration according to claim 1, wherein the whole-process multi-parameter monitoring device simulates injection in different types of well patterns, a mock sequestration system includes a vertical well, a horizontal well, and a full-scale well casing; the full-scale well casing is arranged in a middle of the reactor cover, and the full-scale well casing comprises a full-scale well and one or more of a high-pressure endoscopic imaging system, a grit height detection system, and the heating circulation pipe; well holes are formed on a wall of the full-scale well casing, a drainage hole is formed below the full-scale well casing to discharge excess water in the full-scale well casing, a stainless steel screen is wrapped at the drainage hole to prevent sand in drained water from damaging pipe and valve parts during drainage, and a damping coil is further mounted at the drainage hole to stabilize a high-pressure water flow discharged from the high-pressure reactor to avoid jetting; the heating circulation pipe is arranged in the full-scale well casing to prevent formation of a hydrate in a well bore during simulation of low-temperature high-pressure sequestration resulting in impacts on illumination and observation in the well bore; the high-pressure endoscopic imaging system is arranged in the full-scale well casing to observe the fluid flowing into the well casing through a porous medium; the grit height detection system is arranged at a bottom of the full-scale well casing to monitor accumulation of the porous medium in the full-scale well casing; in the reactor body, the vertical well is arranged perpendicularly to a wall surface of the reactor cover, and the horizontal well is arranged perpendicularly to a wall surface of the reactor body; the vertical well and the horizontal well are connected to a liquid injection module through external pipes; the optical fiber sensors are arranged around the full-scale well casing to monitor well casing deformation; and in the mock sequestration system, a three-phase separator and a gas recovery device are mounted at an outlet of generated gas to treat tail gas.

10. A method for assembling the whole-process multi-parameter monitoring device for simulating the $CO_2$ geological sequestration according to claim 1, the method comprising following steps:
- step 1: arranging different types of injection wells and sensors on the reactor cover, arranging corresponding sensors around the confining pressure rubber bucket, checking whether the sensors at measuring points are firmly mounted or are missing, and measuring whether an insertion depth of each of the measuring points meets a requirement;
- step 2: turning over the reactor cover so that a bottom of the reactor cover faces upward, mounting the confining pressure rubber bucket on the reactor cover in a manner of aligning the confining pressure rubber bucket with the reactor cover, filling the confining pressure rubber bucket with a porous medium layer by layer, and tamping the porous medium according to a target requirement;
- step 3: after the filling is completed, arranging the temperature control system, part of components of the fluid injection system, and the plug assembly at an upper end of the confining pressure rubber bucket, and pre-tightening and fixing the reactor cover and the plug assembly to form a built-in model; turning over the built-in model by 180 degrees again so that a top of the reactor cover faces upward; and
- step 4: hoisting the built-in model into the reactor body, and closing and locking the snap ring, to complete assembly of a mock reactor.

11. A method for simulating $CO_2$ geological sequestration and monitoring changes of physical parameters in a reservoir with a progress of $CO_2$ sequestration and stress loading in different directions using the whole-process multi-parameter monitoring device for simulating the $CO_2$ geological sequestration according to claim 1, the method comprising following steps:
- step 1: preparing the reservoir according to differences of physical parameters of natural reservoirs, wherein during the preparation of the reservoir, acoustic dipoles are pre-buried in the reservoir at a same height as the plurality of resistivity electrodes, and optical fiber sensors are pre-buried in the reservoir;
- step 2: turning on the temperature control system and the fluid injection system, checking air tightness of the whole-process multi-parameter monitoring device, introducing nitrogen gas into the high-pressure reactor through the fluid injection system until an internal pressure of the high-pressure reactor reaches a target pressure; then closing valves on the high-pressure reactor, turning on a confining pressure tracking pump and the axial pressure tracking pump, restoring an in-situ stress condition of the reservoir, and controlling a pressure difference between an interior and an exterior of the confining pressure rubber bucket to be 1 MPa to 3 MPa to prevent the confining pressure rubber bucket from being damaged; observing a pressure change, wherein a pressure drop not greater than 0.01 MPa/h indicates that the device has good air tightness, and subsequent experiments are carried out;
- step 3: releasing the nitrogen gas in the high-pressure reactor, introducing deionized water or multi-component salt solutions of different concentrations into the built-in model through the fluid injection system, and maintaining a pressure to ensure that pores in the reservoir are all filled with the deionized water; then introducing $CO_2$ gas into the built-in model at a constant rate through the fluid injection system until a target pressure is reached; at the same time, monitoring a change of a resistivity in the reservoir by using the electrical resistance tomography sensor and calculating a solubility of $CO_2$; obtaining changes of physical and chemical properties in the reservoir at an initial moment of the $CO_2$ sequestration; ensuring that temperatures inside and outside the high-pressure reactor each reach a target required temperature, monitoring a migration path and a distribution law of $CO_2$ in the high-pressure reactor in real time by using the electrical resistance tomography sensor, and monitoring mechanical changes at positions in the reservoir by using the optical fiber sensors, wherein the optical fiber sensors are at the same height as the resistivity electrodes, and the optical fiber sensors are configured to obtain in real time changes of mechanical properties of the reservoir with a $CO_2$ sequestration process; monitoring an axial deformation of the reservoir by using the axial pressure tracking pump; and
- step 4: adjusting a confining pressure in real time to prevent deformation of the confining pressure rubber bucket, wherein when a pressure drop in the reservoir is less than 0.05 MPa/12 h, the $CO_2$ sequestration is determined to be complete.

* * * * *